United States Patent [19]

Omley

[11] 4,416,275

[45] Nov. 22, 1983

[54] APPARATUS FOR APPLYING A URINE RECEPTACLE TO A MALE

[76] Inventor: Herbert A. Omley, P.O. Box L-2, Wickenburg, Ariz. 85358

[21] Appl. No.: 332,938

[22] Filed: Dec. 21, 1981

[51] Int. Cl.$^3$ .............................................. A61B 17/00
[52] U.S. Cl. ........................... 128/303 A; 128/303.11; 29/235
[58] Field of Search ..................... 128/303 A, 127, 17, 128/326, 345, 303.11; 433/3, 4; 29/235; 269/156

[56] References Cited

U.S. PATENT DOCUMENTS

| | | | |
|---|---|---|---|
| 1,273,480 | 7/1918 | Griffith . | |
| 1,328,624 | 1/1920 | Graham | 128/345 |
| 2,447,474 | 8/1948 | Hammond | 128/319 |
| 2,528,508 | 11/1950 | Gabel | 128/303 |
| 2,601,547 | 6/1952 | Minock | 128/326 UX |
| 2,844,144 | 7/1958 | Perdue | 29/235 |
| 3,138,160 | 6/1964 | Stoutenburgh | 128/295 |
| 3,409,013 | 11/1968 | Berry | 128/326 |
| 3,526,227 | 9/1970 | Appelbaum | 128/295 |
| 3,750,652 | 8/1973 | Sherwin | 128/17 |
| 4,154,242 | 5/1979 | Termanini | 128/349 |
| 4,261,089 | 4/1981 | Taylor | 29/235 |

Primary Examiner—Richard J. Apley
Assistant Examiner—J. L. Kruter
Attorney, Agent, or Firm—Warren F. B. Lindsley

[57] ABSTRACT

A pneumatic apparatus for applying a self-carried urine receptacle snugly on the penis of a human with little danger of involuntary leakage and employing an annular expandable ring for applying to the penis for affixing the receptacle thereto.

11 Claims, 11 Drawing Figures

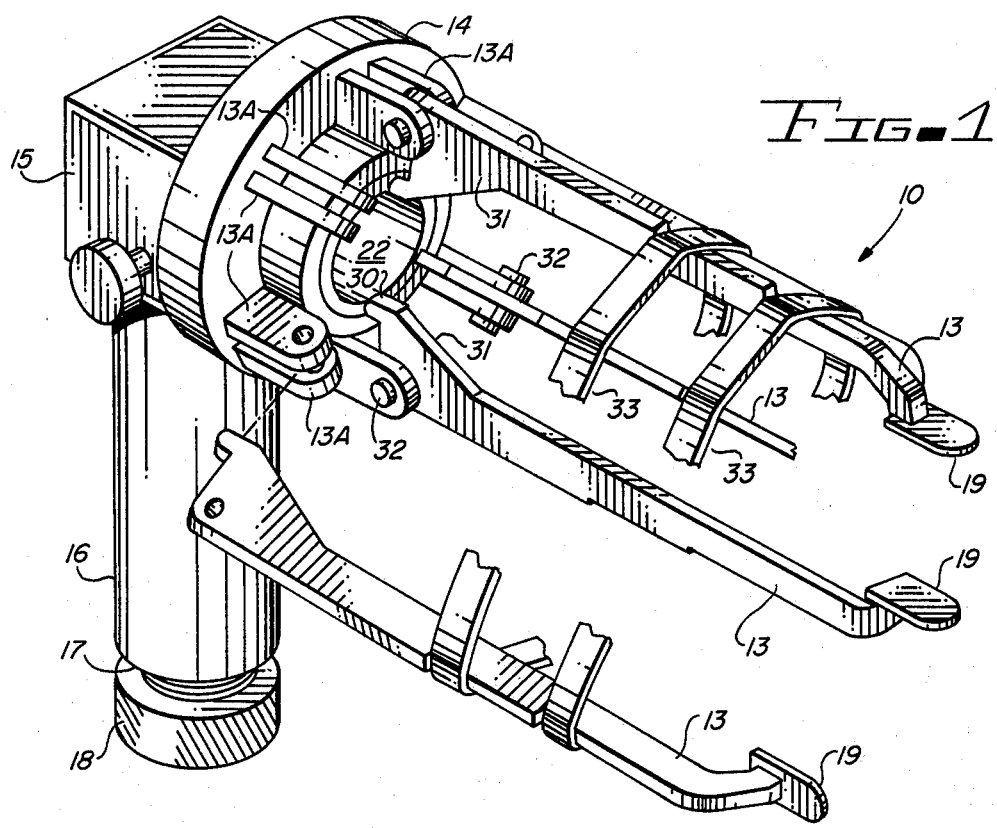
FIG-1
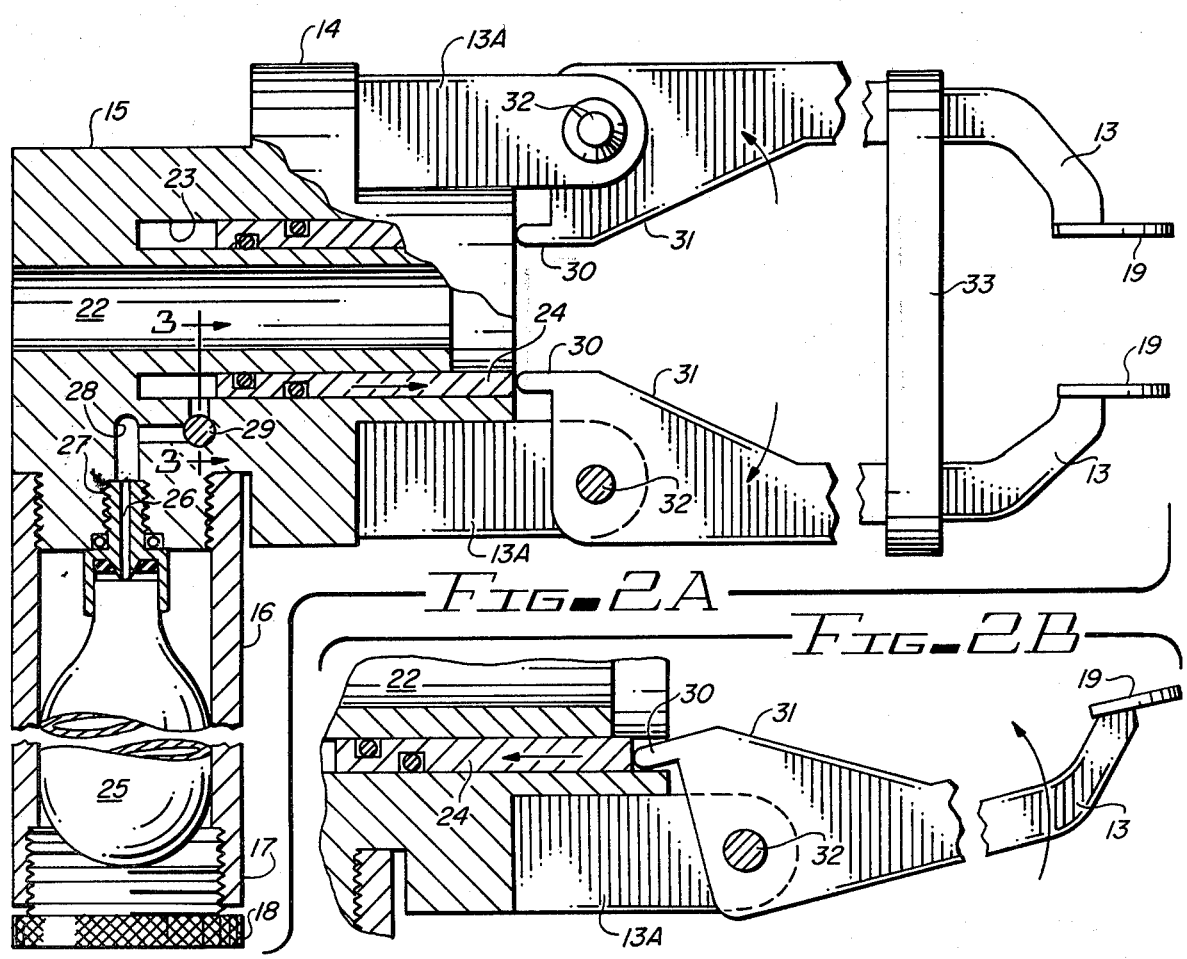
FIG-2A
FIG-2B

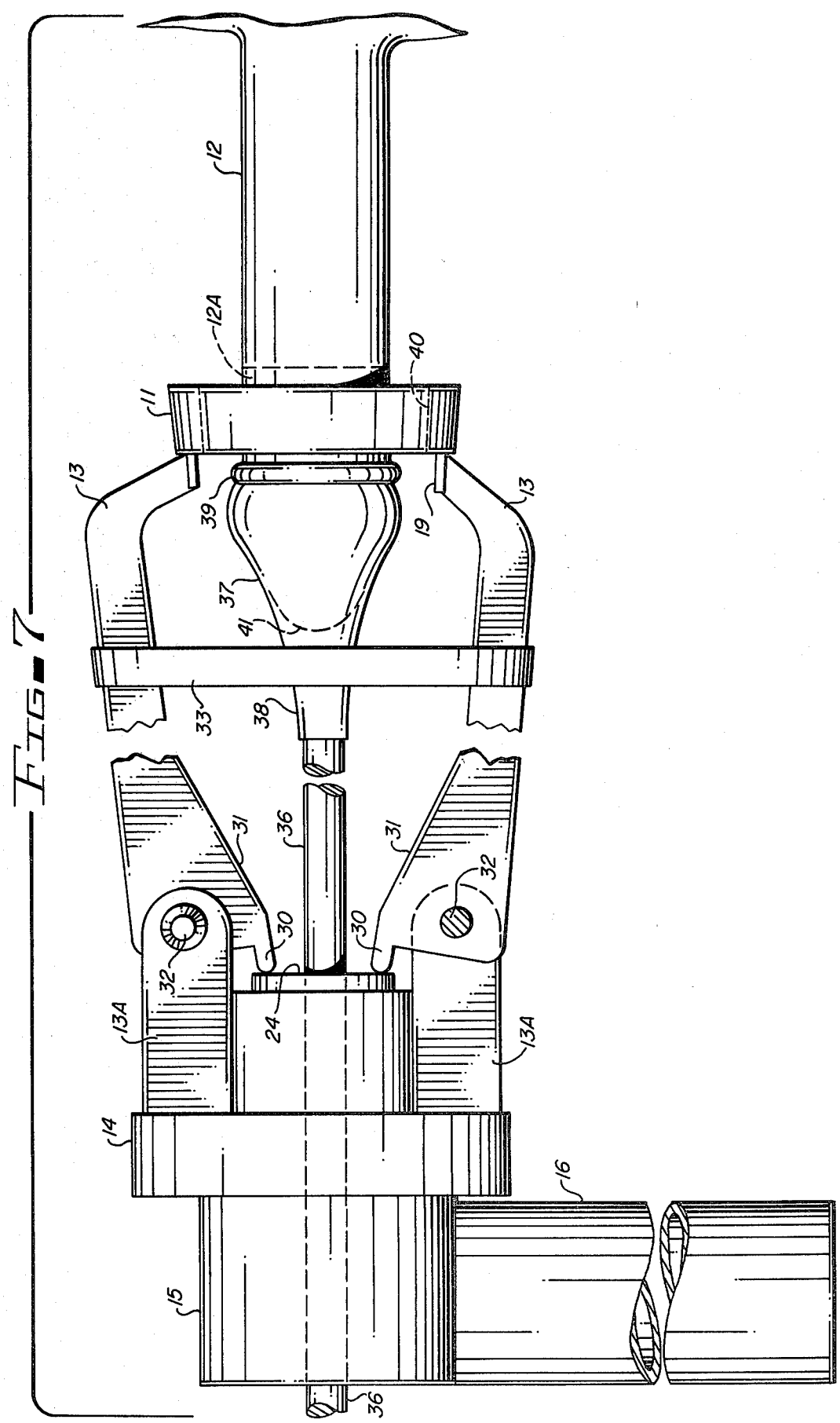

APPARATUS FOR APPLYING A URINE RECEPTACLE TO A MALE

BACKGROUND OF THE INVENTION

This invention relates to apparatus and objects to be used therewith for applying self-carried urine receptacles snugly on the penis of a human with little or no danger of involuntary leakage, whether or not the user is ambulatory or confined to his bed.

FIELD OF THE INVENTION

This invention is particularly directed to an elastic annular expandable ring for use with a urine receptacle and a novel appliance for expanding the ring and applying it to the penis for use in securely affixing a urine receptacle to a user.

DESCRIPTION OF THE PRIOR ART

Although urinary weaknesses have occurred in the male, particularly the young and the old, probably from the beginning of time, it is only recently that a serious attempt has been made to aid the wearer of a urine receptacle in maintaining a leakproof arrangement whether he is ambulatory or bed confined.

U.S. Pat. Nos. 1,273,480; 2,379,346; and 2,699,781 all teach penile type collectors which employ drain valves. U.S. Pat. No. 1,273,480 also teaches the use of a reinforcing band adapted to encircle the urine receptacle at some point remote from the end of the penile gland.

U.S. Pat. Nos. 3,138,160 and 3,526,227 teach the use of a resilient structure for encircling the outside of urine receptacles at some point remote from the end of the penile gland to resiliently engage and retain these receptacles in place.

U.S. Pat. Nos. 3,409,013 and 3,750,650 disclose instruments for producing expansion-retraction movements.

U.S. Pat. No. 4,154,242 discloses a catheter for effecting complete drainage of a bladder.

U.S. Pat. Nos. 2,447,474 and 2,528,508 disclose rubber ring expandable tools.

None of these patents disclose a satisfactory means for attaching a suitable urine receptacle to a male patient which is leakproof and completely functional, whether the user is ambulatory or bed confined.

SUMMARY OF THE INVENTION

In accordance with the invention claimed, a new and improved urinary appliance and device for applying it to a male user is provided which assures the user of a substantially leakproof arrangement and which can be readily applied with less difficulty than similar appliances of the prior art.

It is, therefore, one object of this invention to provide a device or apparatus which may be conveniently applied and used by male incontinents, either ambulatory or bedridden, which is substantially leakproof.

Another object of this invention is to provide a new and improved annular resilient ring for encircling and firmly gripping the penis over which the mouth of a urine receptacle may be securely affixed in a leakproof manner.

A further object of this invention is to provide a new and improved tool for use in grabbing and holding the glans penis while applying an improved annular ring to the shaft of the penis in such a manner that the adhesive surface of the inner periphery of the ring is kept from contacting the undesirable portions of the body.

A still further object of this invention is to provide a new and improved ring expander for use with a tool for holding the glans penis.

A still further object of this invention is to provide a readily usable urinary appliance and tool for application which may be used with confidence in obtaining a leakproof arrangement.

Additional objects and advantages of the invention will become apparent as the following description proceeds and the features of novelty which characterize the invention will be pointed out with particularity in the claims annexed to and forming a part of this specification.

BRIEF DESCRIPTION OF THE DRAWINGS

The present invention may be more readily described with reference to the accompanying drawings in which:

FIG. 1 is a perspective view of a resilient ring expanding apparatus constructed in accordance with the invention;

FIG. 2A is a partial broken away cross-sectional view of FIG. 1 showing the fluid mechanism for actuating the device;

FIG. 2B is a partial cross-sectional view of one of the fingers of the apparatus shown in FIGS. 1 and 2 in its retracted position;

FIG. 7 is a partial perspective view of the apparatus of FIG. 1, ring of FIG. 4 and tool of FIG. 5 being used in applying a resilient ring to a male.

DESCRIPTION OF THE PREFERRED EMBODIMENT

Figure 3:
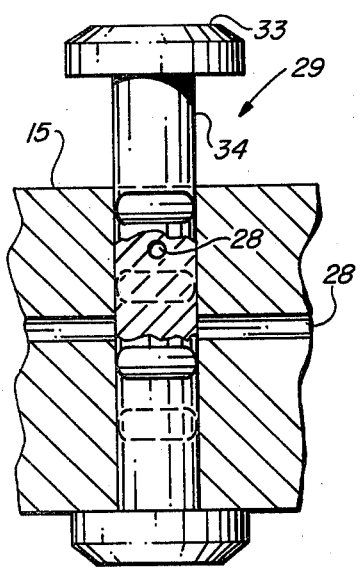
FIG. 3 is a cross-sectional view of FIG. 2A taken along the line 3—3.
Figure 4:
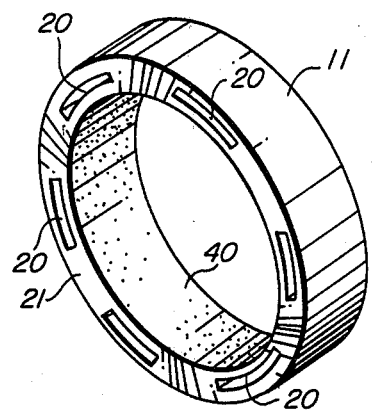
FIG. 4 is a perspective view of an expandable ring for applying to the shaft of the penis of a user with the disclosed apparatus.

Referring more particularly to the drawings by characters of reference, FIGS. 1–3 disclose an instrument or apparatus 10 for applying a resilient, elastic, expandable ring 11, as shown in FIG. 4, to a shaft 12 (FIGS. 6A–6D) of the penis of a human user. This instrument comprises a plurality of arms of jaws 13, each spacedly and pivotally mounted on ears or arms 13A extending laterally from and around the flat surface of a circular supporting disk 14. Disk 14 comprises a part of an integral housing 15, part of which is mounted to extend substantially perpendicular to the direction of jaws 13 and forming a grip or handle 16 of the apparatus for the convenience of a user.

As noted from FIGS. 1 and 2A of the drawings, handle 16 of housing 15 comprises a hollow configuration arranged to be closed at its open end 17 by a plug 18 which threadedly engages the interior of the open end 17 of the handle.

The opposite or free ends of jaws 13 are provided with pads or fingers 19 which are arranged to extend into cooperating grooves or slots 20 spacedly formed in end 21 of ring 11, as shown in FIG. 4. Fingers 19 are mounted so as to extend parallel with the longitudinal axis of disk 14 on which the jaws are mounted. Thus, in the retracted position of fingers 19, they are arranged to extend into slots 20 of ring 11 to firmly grip ring 11 so that it may be expanded by apparatus 10.

It should be noted from FIGS. 1 and 2A of the drawings that an opening 22 is arranged to extend through housing 15, the longitudinal axis of which is coaxially aligned with the longitudinal axis of disk 14 and jaws 13.

A further cylindrical opening 23 is arranged to extend coaxially with and around the periphery of opening 22 in which a ring shaped piston 24 is mounted for reciprocal movement.

As shown in FIG. 2A, a canister 25 of fluid under pressure, such as air or any other suitable gas, is replaceably mounted in the open end 17 of handle 16 which, when mounted therein, places the gas under pressure in the canister in communication with the left end of opening 23 through a passageway 26 in plug 27 and a passageway 28 in housing 15.

A slidable valve means 29 mounted in passageway 28, shown in more detail in FIG. 3, controls the flow of gas under pressure from canister 25 to the left end of piston 24, as shown in FIG. 2A. This valve when open, as shown in FIG. 3, connects gas under pressure in passageway 28 to the left side of piston 24 to move it to the right. This movement of piston 24 engages and biases prongs 30 on the ends 31 of jaws 13 to cause each of them to pivot about their pins 32. This action moves fingers 19 generally radially away from each other at their other ends against the biasing action of a suitable means which, for example, may comprise a pair of rubber bands 33 which encompass the outer periphery of jaws 13 and the biasing effect of ring 11.

When the pressure is reduced or relieved in passageway 28 upon the movement of slide valve 29 to a position opposite to that shown in FIG. 3 by finger pressure on the end 33 of shaft 34 moving end 33 toward housing 15, the gas in cylinder or opening 23 is released to the atmosphere along one end of the stem of valve 29 in a well known manner.

The biasing effect of rubber bands 33 and ring 11 then moves jaws 13 toward each other. This action pivots jaws 13 about their pins 32 causing prongs 30 of jaws 13 to move piston 24 to the left, as shown in FIG. 2B.

Thus, through the use of slide valve 29, fluid pressure may be applied to instrument 10 to spread the free ends of jaws 13 apart and upon the release of that pressure, the rubber bands 33 and ring 11 return piston 24 to its unbiased position and fingers 19 and jaws 13 to their unbiased position, shown in FIG. 2A.

Figure 5:
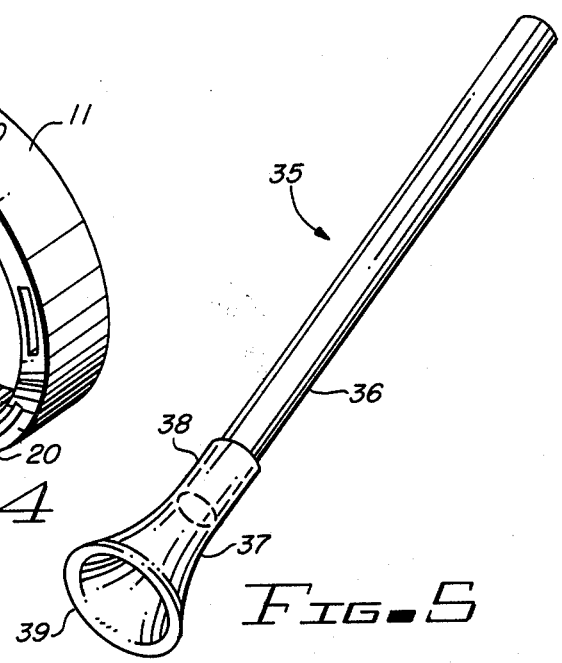
FIG. 5 is a perspective view of a tool for attaching to and holding the glans penis of a user.

In order to use instrument 10 in applying a urinary receptacle to a male, a suitable tool, such as a glans grabber 35 shown in FIG. 5, is employed. This tool comprises a rod 36 to one end of which is applied a resilient funnel-shaped member 37. The spout end 38 of member 37 is telescopically fitted over end end of rod 36. The flared end 39 of the funnel-shaped member 37 is rolled over on itself.

Figure 6A:
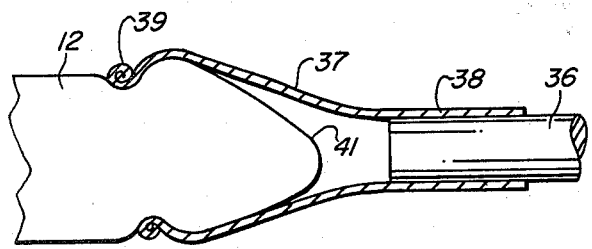
FIG. 6A is a partial cross-sectional view of the tool shown in FIG. 5 in place on the user.

This tool is used to grab the glans penis and hold the penis in an extended position by aligning the end of tool 35 with the end of shaft 12. The glans penis will penetrate into the funnel-shaped member 37, as shown in FIG. 6A. The rolled end of member 37 is then unrolled onto the glans penis sufficient distance to firmly grip it.

It should be noted that it is very difficult to apply any form of a urinary receptacle to the shaft of the penis of a human, whether young or old, since this organ is usually very pliable or flaccid. In order to accomplish such a task, it is necessary to hold the male organ in an extended position from the glans penis and, at that time, attach the urinary receptacle. Thus, tool 35 plays an important part in the proper use of apparatus 10.

Ring 11 is also provided with an adhesive surface 40 on its inner periphery which is used to grip the surface of shaft 12 of the penis when applied thereto. As noted from FIG. 6D, the slotted end of ring 11 may be tapered away from the shaft to aid in moving the flared end 44 of the funnel-shaped end 43 over it, as later explained.

In order to reduce or eliminate any irritation on the shaft of the penis at the point at which the ring is to be adhesively attached, an anti-irritant 12A may be applied to the skin of shaft 12 of the penis; one such material on the market comprises a composition employing Isopropanol, Butyl, Mono Ester and Dimethyl Phthalate.

Further, it should also be noted that the material of which ring 11 is formed should be an expandable rubber, plastic or other suitable material that has a memory and will return to its normal position after expansion. It should be formed of a low durometer material known in the trade as having a hardness A of 10 to 30. This material will not apply an undue pressure to the shaft of the penis so as to interfere with blood flow or any other normal function thereof.

OPERATION

Figure 6B:
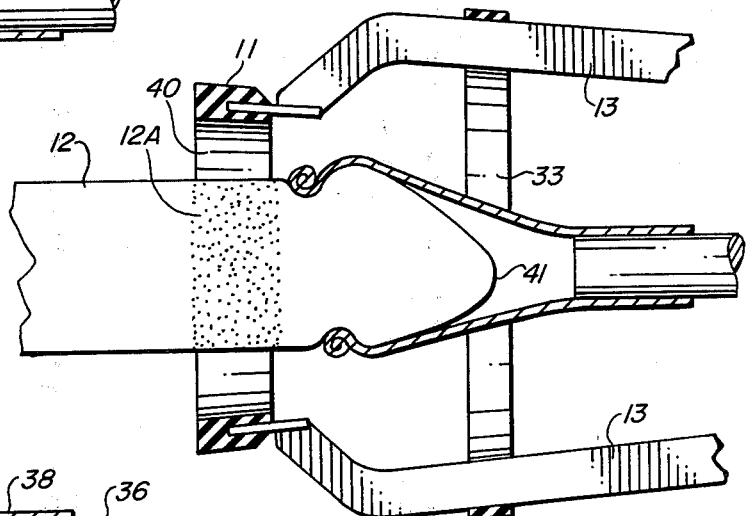
FIG. 6B is a partial cross-sectional view of the apparatus shown in FIG. 1 together with the ring shown in FIG. 4 in its ring expanded position in place over the tool shown in FIG. 6A.

In the normal procedure for applying a urinary receptacle to the shaft of the penis of a user employing the claimed invention, the user inserts fingers 19 of jaws 13 of apparatus 10 when in its unbiased condition into slots 20 of ring 11 to firmly hold the ring when it is expanded, as shown in FIG. 6B.

Ring 11 is expanded by the use of gas pressure from canister 25 to move piston 24 to the right, as shown in FIG. 2A, to spread fingers 19 away from each other.

Tool 35 is then applied to the glans penis of the user by aligning the end of tool 35 with the end of shaft 12. The glans penis should penetrate into the funnel-shaped member 37, as shown in FIG. 6A. At this point, the rolled end of member 37 is unrolled onto the glans penis a sufficient distance to firmly grip it. The user or attendant then, by means of tool 35, holds the shaft of the penis in its extended position.

With ring 11 expanded, instrument or apparatus 10 is then longitudinally moved over the free end of tool 35, with the other end of rod 36 now being attached to the user, passing through the opening between fingers 19 of jaws 13, ring 11 which is in fingers 19 and in the expanded state and through opening 22 in housing 15, as shown in FIG. 7. Apparatus 10 is moved along rod 36 until the expanded ring 11 is at a point spaced approximately a quarter of an inch from the glans penis on shaft 12 and the flared end 39 of funnel 37 of tool 35, as shown in FIG. 6B. The anti-irritant 12A is then applied around the penis at the point ring 11 is to be attached.

Figure 6C:
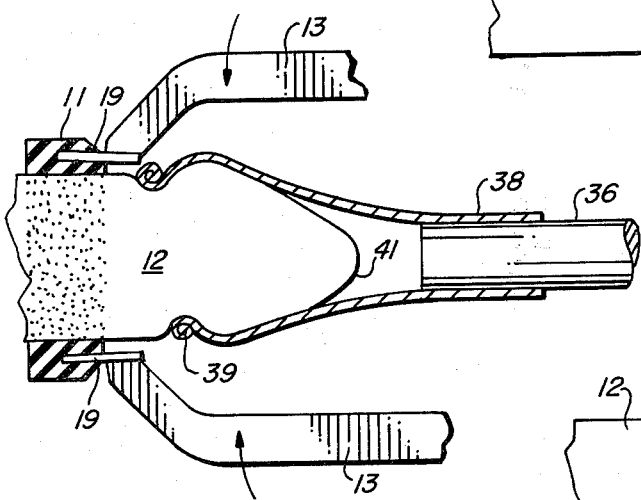
FIG. 6C is a view similar to FIG. 6B with the instrument shown in its retracted position.

The pressure is now relieved from the left side of piston 24, as shown in FIG. 2A, causing rubber bands 33 and ring 11 to bias jaws 13 to their unbiased position, which causes ring 11 to return to its original normal size. At this point, as shown in FIG. 6C, ring 11 snugly adheres to shaft 12 at a distance spaced from end 39 of funnel-shaped member 37 and inwardly along shaft 12 from its tip or end 41. Due to ahdesive 40 on the inner surface of ring 11, ring 11 seals in a leakage proof condition around shaft 12 and forms a solid anchor for the receptacle.

The fingers 19 of instrument 10 are now withdrawn from slots 20 of ring 11, and the instrument is moved longitudinally over and off of tool 35. Tool 35 is then removed from the glans penis of shaft 12 by rolling up flared end 39 of funnel member 37 of the tool.

Figure 6D:
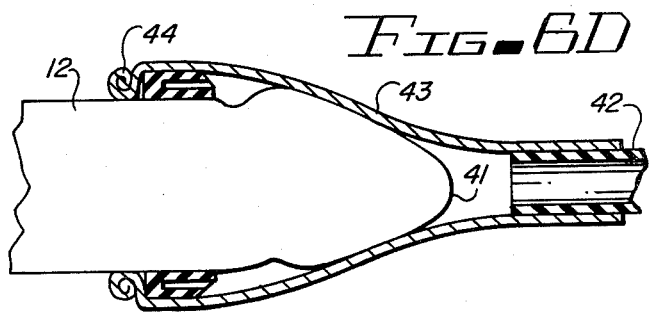
FIG. 6D is a view similar to FIG. 6A showing a drainage appliance or receptacle on the shaft of the male organ over the mounted resilient ring in a leakproof sealing arrangement.

At this point in the procedure, a drainage tube 42, which is provided with a resilient funnel shaped end 43, is applied to the end of shaft 12 in the manner shown in FIG. 6D. The flared end 44 of the funnel-shaped end 43 is expanded and applied over the glans penis 41 and over the now adhesively secured ring 13. Since the flared end 44 was biased outwardly when applied over ring 11 on shaft 12, it will snugly engage shaft 12 over and around ring 11 to form a leakproof seal with it.

If desired, a further securing means such as a piece of tape may be applied over the flared end of member 43 on the outer surface of ring 11. This is not necessary for the appliance to function effectively.

Thus, an appliance and instrument for application is provided for males having a wetting problem which will, in a leakproof manner, attach a urine receptacle to a male.

It will be apparent to those skilled in the art that changes and other modifications may be made to the apparatus shown and described herein without departing from the scope of the appended claims.

What is claimed is:

1. An apparatus for applying an elastic ring to a shaft of a penis for use in attaching a urine receptacle thereto comprising:
    a housing means, an elastic ring having slots on a end surface,
    a plurality of cooperating jaw means pivotally mounted on said housing for movement generally radially relative to each other piston means,
    each jaw means having an outwardly directed finger means at the end of the jaw remote from its pivotal connection for engaging slots in said end surface of the said elastic ring,
    a first means mounted on said jaw means for biasing said jaw means radially inwardly to a predetermined position relative to each other so that the fingers on said jaws can penetrate the slots,
    a second means mounted within said housing for spreading the jaws radially outwardly against the biasing action of said first means after gripping the associated ring to expand the ring to a predetermined diameter, and
    an opening means extending through said housing means axially aligned with the longitudinal axis of the ring for receiving therethrough in a direction extending outwardly of said finger means a tool means for holding the glans penis while the expanded ring is placed thereover and while the jaw means are sequentially biased toward each other to position the ring firmly around the shaft of the penis.

2. The apparatus set forth in claim 1 wherein:
    said first means comprises at least one resilient band mounted around said jaw means for biasing the jaw means toward each other.

3. The apparatus set forth in claim 1 wherein:
    said housing comprises a handle extending laterally of the longitudinal axis of said jaw means, fluid pressure means in said housing for actuating said piston means to a given position.

4. The apparatus set forth in claim 3 wherein:
    said fluid pressure means comprises a canister of gas under pressure mounted in said handle.

5. The apparatus set forth in claim 1 wherein:
    said second means comprises a piston slidably mounted within said housing,
    said piston, when moved to a given position, engaging said jaw means for pivoting them radially outwardly of each other, and
    fluid pressure means mounted in said housing for actuating said piston means to a given position.

6. The apparatus set forth in claim 5 wherein:
    said piston means comprises a ring-shaped member mounted in a cylinder in said housing, which cylinder is coaxially arranged with said opening.

7. The apparatus set forth in claim 5 wherein:
    said piston engages said jaw means adjacent their pivotal connections for biasing radially outwardly from each other.

8. The apparatus set forth in claim 5 wherein:
    said jaw means are provided with prongs adjacent their pivotal connections which lie within the path of movement of said piston means and are engaged by said piston means to pivotally move said finger means outwardly from each other.

9. The apparatus set forth in claim 1 in further combination with:
    an elastic ring,
    said ring having slots spaced formed around one of its ends for receiving the finger means of said jaw means when they are in said predetermined position.

10. The apparatus set forth in claim 5 in further combination with:
    an elastic ring,
    said ring having slots spaced formed around one of its ends for receiving the finger means of said jaw means when they are in said predetermined position.

11. The apparatus set forth in claim 10 wherein:
    said ring is provided with an adhesive, non-irritating to skin surface around its inner periphery.

* * * * *

UNITED STATES PATENT OFFICE
CERTIFICATE OF CORRECTION

Patent No. 4,416,275          Dated November 22, 1983

Inventor(s) Herbert A. Omley

It is certified that error appears in the above-identified patent and that said Letters Patent are hereby corrected as shown below:

Claim 1, line 8, after "other" and before "piston" insert ---,---;

Claim 1, line 10, after "jaw" insert ---means---.

Signed and Sealed this

Twenty-fourth Day of July 1984

[SEAL]

Attest:

GERALD J. MOSSINGHOFF

Attesting Officer          Commissioner of Patents and Trademarks